United States Patent [19]

Brackenridge et al.

[11] Patent Number: 5,055,235
[45] Date of Patent: Oct. 8, 1991

[54] BROMINATION PROCESS

[75] Inventors: David R. Brackenridge; William T. Murray, both of Baton Rouge, La.

[73] Assignee: Ethyl Corporation, Richmond, Va.

[21] Appl. No.: 628,331

[22] Filed: Dec. 12, 1990

[51] Int. Cl.$^5$ ............................................. C09K 21/00
[52] U.S. Cl. .................................... 252/609; 252/601; 570/206; 570/210; 568/56; 568/639; 568/645; 568/647
[58] Field of Search ................ 570/206, 210; 252/601, 252/609; 260/650

[56] References Cited

U.S. PATENT DOCUMENTS

| Re. 32,606 | 2/1988 | Stepniczka | 568/779 |
|---|---|---|---|
| 2,033,612 | 3/1936 | Clark et al. | 260/161 |
| 2,244,284 | 6/1941 | Britton et al. | 260/640 |
| 2,607,802 | 8/1952 | Britton et al. | 260/544 |
| 2,979,637 | 4/1961 | Asadorin | 260/650 |
| 3,062,899 | 11/1962 | Sax | 260/650 |
| 3,141,860 | 7/1964 | Sauer et al. | 260/33.8 |
| 3,232,959 | 2/1966 | Hahn et al. | 260/389 |
| 3,285,965 | 11/1966 | Jenkner | 260/612 |
| 3,331,797 | 7/1967 | Kopetz et al. | 260/28.5 |
| 3,591,645 | 7/1971 | Selwitz | 260/650 |
| 3,752,856 | 8/1973 | Nagy et al. | 260/612 |
| 3,763,248 | 10/1973 | Mitchell | 260/649 |
| 3,833,674 | 9/1974 | Brackenridge | 260/649 |
| 3,911,033 | 10/1975 | Schaffner et al. | 260/649 |
| 3,965,197 | 6/1976 | Stepniczka | 260/623 |
| 3,969,387 | 5/1976 | Brackenridge | 260/612 |
| 4,072,658 | 2/1978 | Okamoto et al. | 260/49 |
| 4,287,373 | 9/1981 | Garman et al. | 568/639 |
| 4,521,633 | 6/1985 | Pedjac | 568/639 |
| 4,666,947 | 5/1987 | Brichta et al. | 521/79 |
| 4,717,776 | 1/1988 | Brackenridge et al. | 568/637 |
| 4,740,629 | 4/1988 | Brackenridge et al. | 568/639 |
| 4,814,525 | 3/1989 | Rule et al. | 570/203 |
| 4,925,994 | 5/1990 | Mais et al. | 570/210 |
| 4,983,781 | 1/1991 | Desmurs et al. | 570/210 |
| 4,990,707 | 2/1991 | Mais et al. | 570/210 |

FOREIGN PATENT DOCUMENTS

| 708209 | 4/1965 | Canada . |
| 0265150 | 4/1988 | European Pat. Off. . |
| 2521926 | 4/1976 | Fed. Rep. of Germany . |
| 2950877 | 6/1981 | Fed. Rep. of Germany . |
| 87752B49 | 9/1979 | German Democratic Rep. . |
| 51-73548 | 6/1976 | Japan . |
| 52-39639 | 3/1977 | Japan . |
| 116332 | 3/1977 | Japan . |
| 116333 | 3/1977 | Japan . |
| 116334 | 11/1978 | Japan . |
| 56-70060 | 6/1981 | Japan . |
| 981833 | 1/1965 | United Kingdom . |
| 991067 | 5/1965 | United Kingdom . |
| 1411524 | 10/1975 | United Kingdom . |
| 1472383 | 4/1977 | United Kingdom . |

OTHER PUBLICATIONS

Inaba et al., In the J. Org. Chem., 49 (12), 2093-8, 1981.
Corey et al., J. Organomet. Chem. 210(2), 149-161, 1981.
Gassman et al., In J. Org. Chem., 47 (20), 4002-4, 1982.
CAS Registry Handbook, p. 632RL.
Chemical Abstracts, vol. 98, 1983 at 98:160866p.

Primary Examiner—Robert L. Stoll
Assistant Examiner—N. Bhat
Attorney, Agent, or Firm—David E. LaRose

[57] ABSTRACT

A process is disclosed for preparing a mixture of brominated, non-condensed ring polyaromatics, which process features multiple bromination temperatures and multiple catalyst additions for brominating the precursor non-condensed ring polyaromatic. The mixture has an average bromine number of about 6 to about 8 bromine atoms per molecule, a low melting point range, and a low amount of light end impurities.

22 Claims, No Drawings

BROMINATION PROCESS

BACKGROUND

This invention relates to a flame retardant product comprising a novel mixture of halogenated polyaromatic compounds having a low melting point range and the process therefor.

Mixtures of brominated non-condensed ring polyaromatics are known. For example, brominated diphenyl oxide mixtures having an average bromine number of from 7.0 to about 7.7 are sold commercially as flame retardants for use in thermoplastic formulations. These mixtures conventionally contain 0–2 weight percent hexabromodiphenyl oxide, 40–55 weight percent heptabromodiphenyl oxide, 30–40 weight percent octabromodiphenyl oxide, 5–15 weight percent nonabromodiphenyl oxide and 0–2 weight percent decabromodiphenyl oxide. Other brominated non-condensed ring polyaromatic mixtures are disclosed in: U.S. Pat. No. 3,833,674; U.S. Pat. No. 4,717,776; and U.S. Pat. No. 4,740,629.

The particular distribution of the various bromo homologs in the mixture will determine the mixture's average bromine number and its possible effect on the physical properties of articles made with thermoplastic formulations containing such mixtures. It is generally desirable to have a high average bromine number since the amount of bromine in the mixture is directly tied to the flame retardant effect per unit weight of the mixture in the formulation. Obtainment of high average bromine number has heretofore been accomplished by producing mixtures which contain large amounts of the hepta- and octabromo homologs. While these higher average bromine numbers are beneficial in regards to minimizing the amount of mixture needed to obtain a certain flame retardancy level, the use of large amounts of hepta- and octabromo homologs is not without a significant penalty. It has been found that such homologs contribute to a reduction in an articles, impact strength, which reduction is similar to that which occurs when a filler, e.g. talc, $Mg(OH)_2$, ZnO, etc. is present in the article. To give the mixture a less filler-type nature, the mixture should contain more of the less brominated homologs, e.g. the penta- and hexabromo homologs, and less of the hepta- and octabromo homologs. The lower brominated homologs, i.e. hexabromo and below, will give the mixture a plasticizer-type component which can be balanced against the filler-type component provided by the higher bromo homologs. A major problem with this approach is that the art has not developed a process which produces a mixture which contains significant amounts of the less brominated homologs and which, has, at the same time, a sufficiently high enough average bromine number. Generally, the mixture containing the less brominated homologs will also contain a higher amount of light-ends which is undesirable from the point of view of thermoplastic formulators.

THE INVENTION

This invention relates to a process for preparing a mixture of brominated non-condensed ring polyaromatics having an average of from about 6 to about 8 bromine atoms per molecule, a low melting point range and a low amount of light end impurities, comprising: adding a first amount of bromine to a reactor initially containing a reaction mass comprising a solvent, a catalytic amount of a first bromination catalyst, and a non-condensed ring polyaromatic; maintaining the reaction mass during the addition of the first amount of bromine at a first bromination temperature; terminating the addition of the first amount of bromine when sufficient bromine has been added to obtain the mixture of polyaromatics having an average of about 4 bromine atoms per molecule of polyaromatic; adding a second bromination catalyst to the mixture; adding a second amount of bromine to the reaction mass while heating the reaction mass to a second bromination temperature; and, after at least substantially all of the bromine has reacted, recovering the brominated non-condensed ring polyaromatic mixture from the reaction mass, the recovered mixture containing more than about 35%, based on gas chromatographic area percent, of a brominated polyaromatic having about 7 bromine atoms per molecule.

The non-condensed ring polyaromatic reactant used in the process of this invention can be represented by the formula

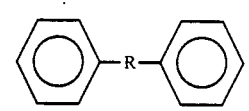

wherein R is an alkylene group containing 1 to 10 carbon atoms, an oxygen atom, a sulfur atom, an oxyalkylene group (—O—R—) of up to 6 carbon atoms, and oxyalkyleneoxy group )—O—R—O—) of up to 6 carbon atoms or a carbon single bond. Preferred R groups are methylene and ethylene which give, respectively, the preferred reactantas, diphenylmethane and 1,2-diphenylethane. Exemplary of other polyaromatic reactants are: diphenyl oxide, diphenyl, diphenylsulfide, 1,3-diphenyoxyethane, 1-methyl-1,2-diphenylethane, 1,3-diphenylpropane, 1,4-diphenylpropane, 1,4-diphenylbutane, 1,6-diphenylhexane, 2,3-dimethyl-1,4-diphenylbutane, 2-ethyl-3-methyl-1,4-diphenylbutane, 2-methyl-1,6-diphenylhexane, 1,9-diphenyklnonane and 1,10-diphenyldecane and the like.

Based upon present day and anticipated market demand for certain mixtures of this invention, diphenyl oxide and 1,2-diphenylethane are the preferred reactants. The diphenyl oxide has been in commercial use for several years and is commercially available. Diphenylal can be produced by various routes. For example, CA 97 3865 Kokai 82/45114) and CA 46 7084g disclose the reaction of benzene and ethylene dihalide in the presence of aluminum trichloride to yield diphenylethane. Another process for producing diphenylalkane includes the oxidative dimerization of toluene at a temperature of at least 400° C. in the presence of a metal oxide catalyst to yield diphenylethane and diphenylalkene. The latter product is then hydrogenated to remove the olefinic unsaturation.

It is not uncommon for the diphenylalkane reactant to be accompanied by various impurities. These impurities often give the final decabromodiphenyl alkane product an off color. Exemplary of these color-causing impurities are diphenylmethane, tetrahydronaphthalene, phenylcyclohexane, and the methyl and ethyl derivatives of 1,2-diphenylethane. Diminishing the impurity content can be accomplished in a conventional manner, for example, the diphenylalkane can be recrystallized or distilled.

The bromination catalysts used in the process of this invention are conventional and are available from commercial sources or can be readily made by those skilled in the art. Bromination catalysts which may be used are Al; $AlCl_3$; $AlBr_3$; Zr; $ZrCl_4$; $ZrBr_4$; $Fe^o$; $FeCl_3$; $FeBr_3$; and a 1:1 ratio of $FeCl_3$:$CH_3NO_2$, $FeBr_3$:$CH_3NO_2$ : or mixtures thereof. The most preferred catalysts are, at least initially in the form of $ZrCl_4$ and $AlC_3$. In a highly preferred embodiment of the invention, $ZrCl_4$ is used as the first bromination catalyst and $AlCl_3$ is used as the second bromination catalyst.

Since the catalytic activity of the catalyst is degraded by contact with water, at least near anhydrous conditions should be present before and during the reaction of the polyaromatic reactant and bromine The catalytic quantities of each bromination catalyst used in the process range from about 1 weight percent to about 15 weight percent of the total weight of the polyaromatic to be brominated. Preferred amounts are within the range of from about 4 weight percent to about 6 weight percent of the total weight of the polyaromatic reactant The solvent used must be one in which the polyaromatic reactant and the mixture of brominated non-condensed ring polyaromatics are substantially soluble. It is a key feature of this invention that the mixture of brominated non-condensed ring polyaromatics has a bromohomolog distribution which contributes to a significant increase in the degree of solubility of the mixture in the solvent at or near the reflux temperature of the solvent. The degree of solubility of the mixture in the solvent is easily determined by the weight percent of the mixture in the solvent. By significant increase in the degree of solubility is meant that the weight percent of the brominated non-condensed ring polyaromatic mixture in the solvent has increased from less than about 20 wt.% to about 40 wt.% or more when the temperature of the solution is about at reflux.

The solvent should also be a liquid during the bromination of the polyaromatic reactant and substantially inert to the process. Generally, halogenated lower alkanes are suitable. Exemplary solvents are methylene bromide, methylene chloride, ethylene dibromide, ethylene dichloride, bromochloroethane, and mixtures thereof. When using ethylene dichloride, process temperatures which promote transhalogenation of the solvent should be avoided. Preferred solvents are methylene bromide, methylene chloride, bromochloromethane, and mixtures thereof. The most preferred solvent is methylene bromide.

The amount of solvent used is that amount which will at least provide a stirrable reaction mass and significant dissolution of the mixture containing the desired bromohomolgs. Generally, from about 300 to about 2000 Ml of solvent per mole of polyaromatic reactant is suitable. Preferably, from about 500 mL to about 1500 mL of solvent per mole of polyaromatic reactant is used, and most preferably, from about 800 mL to about 1200 mL of solvent per mole of polyaromatic reactant is used. It has been found that by utilizing the minimum amount of solvent required to obtain an easily stirred reaction mass and dissolution of the desired bromo-homologs, recovery of a product having an average of from about 6 to about 8 bromine atoms per molecule is greatly enhanced.

The polyaromatic reactant, solvent, and first bromination catalyst can be provided to the reactor in any order and in any combination. A preferred manner of addition is to first add a solution of the solvent and the polyaromatic reactant to the reactor and then to add the first bromination catalyst. It is preferred that the addition of the materials be at a temperature which is at least near the first bromination temperature. Otherwise, the reactor contents may need to be heated, or cooled, as the case may be, to achieve the selected bromination temperature. This is not to say that addition cannot occur at other temperatures. However, when the first amount of bromine is added and/or reacted at low temperatures, e.g. 0° C.-b 10° C., and the reactor contents are cooled, care must be taken to prevent atmospheric moisture from being aspirated into the reactor. The presence of water in the reactor is not desirable as water can deactivate the catalyst. Cooling of the reactor contents may occur naturally by the mixing of the non-condensed ring polyaromatic and solvent, or a cooling medium may be applied to the reactor shell in order to cool the reactor contents.

It is another key feature of this invention that at least a portion of the bromination of the polyaromatic is conducted at a first bromination temperature and at least a portion of the bromination is conducted at a second bromination temperature. Prior to the addition of the first amount of bromine to the reactor, the polyaromatic reactant, solvent and the first catalyst in the reactor are at a temperature which is below about 50° C., and preferably between about 15° C. and about 40° C. If the desired first bromination temperature is different than room temperature, heating or cooling of the polyaromatic reactant, solvent and/or first bromination catalyst may be necessary prior to charging the reactor so as to have the reactor contents at the desired bromine addition temperature. Another method is to charge the three components to the reactor at room temperature and then heat or cool the charge to the desired temperature. During the reactor charging, it is prudent, as before noted, to prevent atmospheric moisture from being aspirated into the reactor.

The addition of the first amount of bromine to the contents of the reactor should occur soon after the polyaromatic reactant, solvent and first bromination catalyst have been charged and the reactor contents are at the first bromination temperature. The first amount of bromine added is that amount which will give the mixture an average bromine number, based upon GC area percent, which is within the range of from about 3.5 to about 4.5.

Subsequent to obtaining the mixture of brominated polyaromatic with about 4 bromine atoms per molecule, the reactor contents are heated to the second bromination temperature for the addition of the second amount of bromine. Heating of the reactor contents may be achieved by supplying heat thereto, recirculating at least a portion of the reactor contents through a heat exchanger, or allowing the heat of reaction to raise the temperature of the reactor contents naturally. The second bromination temperature is preferably in a range of from about 35° C. to about 80° C. and most preferably from about 40° C. to about 50° C. When the reactor contents are at or near the second bromination temperature, the second bromination catalyst then is added to mixture in the reactor followed by the second amount of bromine. Concurrently with the addition of the second amount of bromine, the temperature of the reactor contents is raised from about 40° C. to about 65°-70° C.

While not desiring to be bound by theory, it is believed that a temperature in the range of from about 40° C. to about 70° C. will increase the solubility of the hexabromohomologs in the solvent and increase the tendency to further brominate these hexabromohomologs to the desired degree.

The second amount of bromine which is added to the reaction mass is that amount which will give the recovered mixture an average bromine number, based upon GC area percent, which is within the range of from about 6.0 to about 8.0 and most preferably about 6.5 to about 7.5.

Since all of the bromine which is added to the reactor is reacted, and since it takes one mole of bromine, i.e. $Br_2$, per mole of polyaromatic reactant to effect the placement of one bromine atom on the ring, the total number of moles of bromine added will substantially equal the average bromine number of the recovered mixture. The term "substantially" is used to describe this equality since it is possible that some of the bromine added will be lost from the reaction due to its entrainment in the stream of HBr being evolved from the reactor contents and/or due to any competing side reactions. Generally, the losses are not great, say 0.50 percent of the bromine added. However, to obtain the desired average bromine number, any losses must be made up by the addition of the excess "make-up" bromine. Thus, in most instances the total amount of bromine added will be in slight molar excess of that which equals the average bromine number of the recovered mixture. For example, to obtain an average bromine number of seven, about 7 moles of bromine are usually added. In most instances, from about 6.65 to about 7.05 moles of bromine will be added.

During the bromine addition of the first and second amounts of bromine to the reactor, the bromine is preferably added at a rate which does not cause the reaction mass to overheat and/or does not cause an evolution of by-product HBr which is so great that a safety hazard is created. From a process efficiency standpoint, it is preferable that the addition rate be as rapid as is possible without realization of significant overheating and/or safety problems. Generally for lab scale processes the bromine addition rate is preferably from about 0.2 mL/min to about 1.5 mL/min and most preferably from about 0.3 mL/min to about 0.5 mL/min. Determining the optimum addition rates for large scale processes will be dependent upon reactor configuration, reaction mass size, reactor cooling equipment available and process economics. The optimum addition rate is best determined empirically for each different process size and equipment configuration used.

After the addition of the second amount of bromine is complete, the reaction mass is allowed to undergo a ride period until at least substantially all of the bromine has been reacted. There are two signs that can be used to confirm completion of the bromine reaction. The first sign is the loss of a red color in the reaction mass. Use of this sign for determining ride time is most convenient when carrying out the process in a transparent reactor, such as a laboratory glass flask, or a reactor provided with a sight-glass or other direct or indirect viewing means. A second sign is the cessation of HBr evolution from the reactor contents. This sign is more convenient for use with large scale processes.

The ride time is affected by the temperature of the reactor contents after the bromine addition. Shorter ride times are associated with higher reaction mass temperatures and longer ride times are associated with lower temperatures. It is preferred at the temperature of the reactor contents be within the range of from about 55° C. to about 75° C. during the ride period. Generally, it is not desirable to let the temperature of the reactor contents go above about 80° C. as adverse side reactions or solvent loss can occur. The maximum temperature is somewhat determined by the particular solvent used. For the preferred solvent, methylene bromide, the maximum temperature during the ride time will not exceed about 65° C. The temperature of the reactor contents during the ride time is generally achieved by applying heat thereto.

After the reaction between the bromine and the polyaromatic reactant has at least substantially ceased, the brominated mixture is recovered from the reaction contents. Some of the mixture substituents may be dissolved in the solvent and they need to be at least partially recovered therefrom. One technique that can be used is to contact the reactor contents with a $C_1$ to $C_4$ alkanol. The alkanol acts as a precipitating agent to precipitate at least a portion of the dissolved mixture substituents from the solvent. A preferred alkanol is methanol. The reactor contents and alkanol are brought into contact by adding one to the other. The amount of alkanol used can be within the range of from about 1 to about 3 volumes of alkanol per volume of the reactor contents. There is no real upper limit to the amount of alkanol that can be used, however, secondary considerations, such as reactor size and process economics, will determine the amount which is sensibly used. The lowest amount of alkanol that is used is that amount which is capable of effecting the recovery sought. The temperature at which the reactor contents and alkanol are contacted is not critical and any convenient temperature can be used. Preferred temperatures are within the range of from about ambient temperature to about 65° C. The contact can be maintained up to two hours to insure the highest degree of precipitation of the brominated polyaromatic mixture substituents which were in the solvent. Lesser times can be used since most substituents will precipitate out almost immediately. The resultant solid portion of the reactor contents, which comprises the brominated polyaromatic mixture, is recovered by conventional liquid-solid separation methods, e.g. filtration, centrifugation, etc.

The other technique for recovering the brominated polyaromatic mixture involves flashing the solvent from the reaction mass by contacting the reaction mass with hot water, i.e. water at a temperature sufficient to effect flash vaporization of the solvent from the reaction mass. The remaining residue is comprised principally of the brominated polyaromatic mixture. This method has an added advantage in that the water will deactivate and solubilize the catalyst.

To reduce the impurities in the recovered brominated polyaromatic mixture, the mixture can be washed with alkanol, caustic, water or all three. After washing, the mixture is then dried and milled, if desired, to yield a particulate product.

Another feature of this invention is the obtainment of a product with a low melting point range and a low amount of light end impurities. By "low melting point range" is meant a melting point range for the mixture that is below about 200° C., preferably below about 190° C. and most preferably in the range of from about 100° C. to about 180° C. In comparison, a high melting point range is from about 160° to about 220° C. The product of this invention with a low melting point range is particularly suited to recovery from the solvent by a wiped film evaporator at a temperature in the range of from about 160° to about 210° C.

The light end impurities which are minimal in the product of this invention include brominated benzenes and benzene derivatives. By low amount of light end impurities is meant a mixture containing preferably less than about 1.0 GC area percent light ends and most preferably less than about 0.5 GC area percent. Having a low amount of light end impurities in the flame retardant product reduces the tendency of the flame retardant to cause bloom in flame retardant formulations.

Utilizing the process of this invention, the novel brominated polyaromatic mixtures thus produced are characterized in that:
(1) they have an average bromine number, based upon GC area percent, within the range of from about 6.0 to about 8.0;
(2) heptabromo-homolog in the mixture is present in an amount greater than any other homologs;
(3) the mixture has a low amount of light end impurities; and
(4) the mixture has a low melting point range.

Even though the above specifies that the predominant homolog is the heptabromo-homolog, other bromo homologs will probably be present. For example, when the polyaromatic reactant is diphenyl ethane, tetrabromodiphenyl-ethane, pentabromodiphenylethane, octabromodiphenylethane, nonabromodiphenylethane, and decabromodiphenylethane can be present.

The average bromine number is defined as the average number of bromine atoms per molecule of brominated polyaromatic in the mixture. The average bromine number can be calculated by multiplying the gas chromatographic (GC) area percent or the weight percent of each bromo homolog in the mixture by the number of bromine atoms in that homolog, adding the resulting product and dividing the sum by 100. There will be a slight variation between the average bromine number obtained when using the GC area percent and when using weight percent. This variation can exist because the GC area percent does not always accurately reflect the quantitative relationship between the different bromo homologs in the mixture. The inaccuracy is due to the GC response being different for various of the bromo homologs in the mixture. The variation between GC area percent and weight percent can be resolved by multiplying the GC response factor for each bromo homolog times the GC area percent for that homolog. The product will give the weight percent. For the mixtures of this invention, preferred average bromine numbers, based upon GC area percent, are within the range of from about 5.0 to about 8.0, with an average bromine number of from about 6.0 to about 7.5 being most preferred. Most highly preferred are average bromine numbers of about 6.6 to about 7.1.

For the purposes of obtaining the GC area percents and the identities of the bromo homologs which form the mixtures produced by the process of this invention, a combination of gas chromatography and mass spectrometry can be used. The mass spectrometer is used to identify each bromo homolog and correlate its identity with the particular peak(s) and retention time(s) shown by the gas chromatogram. Standard gas chromatography procedures are used for analyzing the products of this invention.

It is recognized that the GC area percent values for each bromo homolog may vary slightly dependent upon the particular gas chromatograph used and upon the analytical conditions used in operating the gas chromatograph.

The GC response factors used in obtaining the weight percent values recited herein are approximates which are based upon empirical observation and experience in quantifying the bromo homologs in various flame retardants.

| Bromo homolog | Response Factor |
|---|---|
| DPO/DPE-BR$_4$ | 0.85 |
| DPO/DPE-BR$_5$ | 0.85 |
| DPO/DPE-BR$_6$ | 0.9 |
| DPO/DPE-BR$_7$ | 0.9 |
| DPO/DPE-BR$_8$ | 1.0 |
| DPO/DPE-BR$_9$ | 1.1 |
| DPO/DPE-BR$_{10}$ | 1.1 |

More exact response factors can be obtained by conventionally comparing the GC area percents of a known amount of each brominated homolog against one another.

On the basis of GC area percent, a typical bromo homolog distribution for brominated diphenylethane mixtures of this invention is, 0–1 GC area percent pentabromodiphenylethane, 20–30 GC area percent hexabromodiphenylethane, 35–50 GC area percent heptabromodiphenylethane, 20–32 GC area percent octabromodiphenylethane, 2–8 GC area percent nonabromodiphenylethane, and 0–1 GC area percent decabromodiphenylethane. The mixture can also contain some light end impurities, usually less than about 0.5 GC area percent.

When the mixtures are derived from diphenyl oxide a bromo homolog distribution similar to that for diphenylethane can be obtained by use of the process of this invention.

The brominated polyaromatic mixtures produced by the process of this invention are useful as flame retardants in ABS, i.e. acrylonitrile-butadiene-styrene, based formulations. The amount used to achieve the desired flame retarded effect, is generally from about 10 weight percent to about 25 weight percent, based upon the total weight of the formulation. It is preferred that the formulation also contain any of the well known flame retardant synergists which are commonly used with halogen containing flame retardants. Such synergists enhance the flame retardant qualities of the brominated polyaromatics in the mixture and thus enable the use of lesser amounts of the mixture to obtain the desired flame retardant effect. Examples of such synergists are $Sb_2O_3$, $Sb_2O_4$, and $Sb_2O_5$, zinc oxide, zinc borate, various inorganic bismuth compounds and organic compounds, such as, tris-2-chloroethyl-phosphate, tris-2,3-dibromo-propyl-phosphate, etc. The most preferred synergist is $Sb_2O_3$.

The flame retardant synergist will generally be used in an amount, based upon the total weight of the ABS based formulation, which is within the range of from about 2 weight percent to about 6 weight percent. When a flame retardant synergist is used, the amount of brominated polyaromatic mixture used is preferably within the range of from about 10 weight percent to about 20 weight percent.

The ABS resin can be any of those which are denominated by the art as high impact, medium impact, low impact or heat resistant. The ABS resin can be comprised of any suitable proportion of acrylonitrile, rubber or styrene. The resin can also be any of those produced by the well known emulsion, suspension or batch processes. Even further, the resin may have units other than acrylonitrile, butadiene and styrene. For example, methylmethacrylate can be copolymerized therewith. Also, other polymers may be used to modify the ABS resin, such other polymers including modified styrene resins, such as rubber modified polystyrenes, and the styrene containing copolymers, such as the styrene-acrylonitrile copolymers, styrene-butadiene copolymers, styrene-acrylonitrile-α-alkyl styrene copolymers, poly-α-methyl styrene, copolymers of ethylvinylbenzene and divinylbenzene, and the like. The preferred resin is unmodified acrylonitrile-butadiene-styrene. For a further discussion of suitable ABS resins, see Kirk-Othmer *Encyclopedia of Chemical Technology,* 3rd edition, John Wiley & Sons, Vol. 1, pages 442–456, and *Encyclopedia of Polymer Science and Technology,* John Wiley & Sons, Vol. 1, pages 436–444, all of which are incorporated herein by reference as if fully set forth.

The ABS resin substituent used in the formulation will comprise from about 40 to about 90 weight percent of the formulation and preferably from about 50 to about 85 weight percent.

The substituents of the ABS based formulation can be blended one with the other in any order and by way of any conventional technique. A Banbury mixer or twin screw extruder can be used.

The ABS based formulation can also contain conventional additives, for example, plasticizers, pigments, antioxidants, fillers, e.g. talc, glass, etc., UV stabilizers, processing aids and the like.

Conventional article forming techniques can be used to form articles from the above described ABS based formulations. For example injection molding, compression molding, and extrusion molding are all suitable.

The following Examples illustrate some of the features of the inventions hereinabove disclosed and are not to be taken as limiting such inventions.

EXAMPLES

The following equipment was used in Runs 1–32. A 500 mL, 5-necked reaction flask was fitted with a Friedrich's condenser modified for use as a dry-ice/isopropyl alcohol (IPA) cold-finger condenser. The reactor overhead led from the condenser exit to an oil bubbler charged with inert fluorocarbon oil, a safety trap and a tared caustic trap. The dip-leg to the caustic trap was positioned just below the liquid surface; the trap itself was placed on a balance to measure HBr evolution quantitatively with reaction time. Alternatively, the trap could be stirred magnetically if HBr weight was not a concern. A nitrogen line was tied into the overhead, downstream from the condenser. A 3-way Teflon stopcock allowed a $N_2$ purge to maintain positive pressure when HBr flow became weak, thus preventing caustic suck-back. To clear most of the residual HBr from the system, the nitrogen purge could be transferred to the 3-way stopcock on the side-arm of the empty bromine addition funnel. With the stopcock open, the addition funnel, reactor and condenser vapor spaces could be flushed at a controlled rate. The addition funnel itself was fitted with a 2 mm, metered Teflon stopcock. A thermocouple thermowell was placed in the fourth reactor neck; the fifth neck was used for catalyst addition.

EXAMPLE 1

In Runs 1–12 (TABLE I), diphenylethane (DPE) was reacted with 7.0 moles of bromine per mole of DPE in the presence of a first bromination catalyst, $ZrCl_4$, and a second bromination catalyst, $AlCl_3$. The first bromination temperature was about 20°–30° C. and the second bromination temperature was about 40°–70° C. The solvent used was methylene bromide. Run No. 12 was given to illustrate the use of a different first bromination catalyst, i.e. $FeCl_3$.

Runs No. 13–23 were given to illustrate the effect various parameters had on the bromo-homolog distribution of the brominated diphenylethane product. These runs were typical of the effect varying the preferred bromination parameters had on the product bromo-homolog distribution. In Runs 13–15, the moles of bromine per mole of DPE added to the reaction vessel were varied. Runs 16–17 illustrated the effect the bromination temperature had on the bromo-homolog distribution of the product. In runs 18–20, a solvent other than methylene bromide was used. Runs 21–23 utilized less than the preferred amount of catalyst during at least one of the bromination steps.

TABLE I

| Run No. | Catalyst (grams) | DPE (moles) | Br$_2$/DPE Added (moles) | React. Temp. (°C.) | Ride Time (min) | Ride Temp. (°C.) | M.P. (°C.) | Br$_5$ | Br$_6$ | GC Br$_7$ | Area Br$_8$ | Percent Br$_9$ | Br$_{10}$ | Light Ends |
|---|---|---|---|---|---|---|---|---|---|---|---|---|---|---|
| 1 | 1.5<br>1.2 | 0.1 | 4.0<br>3.0 | 19–31<br>45–65 | 120 | 65–75 | 109–170 | 0.6 | 21.5 | 44.4 | 28.8 | 4.3 | tr | 0.3 |
| 2 | 1.0<br>1.1 | 0.1 | 4.0<br>3.0 | 20–30<br>40–65 | 120 | 65–75 | 112–173 | 0.9 | 26.7 | 39.6 | 25.6 | 6.0 | 0.7 | 0.4 |
| 3 | 2.0<br>2.1 | 0.2 | 4.0<br>3.0 | 17–33<br>45–66 | 120 | 60–70 | 120–172 | 0.6 | 24.8 | 44.0 | 31.4 | 5.3 | 0.4 | 0.1 |
| 4 | 7.9<br>8.0 | 0.8 | 4.0<br>3.0 | 20–25<br>45–67 | 120 | 60–63 | 122–190 | 0.8 | 29.7 | 37.8 | 25.0 | 6.0 | 0.5 | 0.1 |
| 5 | 8.0<br>8.0 | 0.8 | 4.3<br>3.0 | 21–26<br>43–67 | 60 | 63–66 | 112–171 | 0.5 | 28.2 | 39.7 | 26.1 | 5.2 | 0.2 | 0.2 |
| 6 | 8.0<br>8.0 | 0.8 | 4.0<br>3.0 | 18–26<br>47–65 | 60 | 60–65 | 120–170 | 0.5 | 26.4 | 40.6 | 26.7 | 5.3 | 0.2 | 0.2 |
| 7 | 8.0<br>8.0 | 0.8 | 4.0<br>3.0 | 20–26<br>44–65 | 60 | 63–64 | 120–172 | 0.5 | 27.9 | 38.6 | 27.0 | 5.7 | 0.3 | 0.1 |
| 8 | 1.0<br>1.0 | 0.1 | 4.0<br>3.0 | 25–30<br>45–65 | 120 | 65–75 | — | 0.9 | 26.8 | 46.5 | 25.3 | 3.1 | tr | 0.3 |
| 9 | 6.0<br>5.9 | 0.6 | 4.0<br>3.0 | 25–28<br>45–65 | 60 | 65–70 | 109–175 | 0.5 | 22.4 | 43.3 | 27.2 | 6.0 | 0.2 | 0.4 |
| 10 | 6.1<br>6.0 | 0.6 | 4.0<br>3.0 | 25–28<br>45–65 | 60 | 67 | 107–173 | 0.6 | 22.0 | 49.3 | 21.9 | 6.0 | 0.2 | 0.4 |
| 11 | 6.1<br>6.0 | 0.6 | 4.0<br>3.0 | 25–30<br>45–65 | 60 | 65–70 | — | 0.6 | 29.0 | 38.3 | 25.8 | 5.9 | 0.3 | 0.3 |
| 12[1] | 0.8 | 0.1 | 4.0 | 22–31 | 64 | 63–75 | 115–173 | 0.6 | 23.8 | 42.8 | 27.3 | 5.1 | 0.3 | 0.2 |

TABLE I-continued

| Run No. | Catalyst (grams) | DPE (moles) | Br$_2$/DPE Added (moles) | React. Temp. (°C.) | Ride Time (min) | Ride Temp. (°C.) | M.P. (°C.) | Br$_5$ | Br$_6$ | GC Area Br$_7$ | Br$_8$ | Percent Br$_9$ | Br$_{10}$ | Light Ends |
|---|---|---|---|---|---|---|---|---|---|---|---|---|---|---|
| | 1.0 | | 3.0 | 52–65 | | | | | | | | | | |

[1]FeCl$_3$ was used in the first bromination step, and AlCl$_3$ was used in the second bromination step.

TABLE II

| Run No. | Catalyst (grams) | DPE (moles) | Br$_2$/DPE Added (moles) | React. Temp. (°C.) | Ride Time (min.) | Ride Temp. (°C.) | M.P. (°C.) | Br$_5$ | Br$_6$ | GC Area Br$_7$ | Br$_8$ | Percent Br$_9$ | Br$_{10}$ | Light Ends |
|---|---|---|---|---|---|---|---|---|---|---|---|---|---|---|
| 13[2] | 1.0 | 0.1 | 4.0 | 20–28 | 48 | 63–65 | 65–170 | 1.9 | 51.5 | 34.7 | 10.5 | 1.0 | — | 0.3 |
| | 1.0 | | 2.5 | 43–66 | | | | | | | | | | |
| 14[2] | 1.1 | 0.1 | 4.0 | 21–29 | 44 | 60–63 | 125–162 | 1.0 | 41.0 | 41.2 | 13.7 | 2.7 | — | 0.3 |
| | 1.0 | | 2.75 | 43–65 | | | | | | | | | | |
| 15[3] | 1.0 | 0.1 | 4.0 | 21–30 | 64 | 63–65 | 137–201 | 0.8 | 25.4 | 31.3 | 29.2 | 11.7 | 1.4 | 0.2 |
| | 1.0 | | 3.2 | 47–65 | | | | | | | | | | |
| 16[4] | 0.9 | 0.1 | 4.0 | 35–40 | 60 | 65 | 93–148 | 1.1 | 27.6 | 42.0 | 24.7 | 3.6 | tr | 1.1 |
| | 1.0 | | 3.0 | 65 | | | | | | | | | | |
| 17[5] | 1.0 | 0.1 | 4.3 | 25–30 | 120 | 65–75 | 110–167 | 1.5 | 41.3 | 35.2 | 17.6 | 3.98 | 0.2 | 0.5 |
| | 1.0 | | 3.0 | 45–55 | | | | | | | | | | |
| 18[6] | 1.0 | 0.1 | 4.0 | 25–30 | 60 | 65 | 113–175 | 1.1 | 38.9 | 26.6 | 23.0 | 8.7 | 1.2 | 0.6 |
| | 1.0 | | 3.0 | 45–65 | | | | | | | | | | |
| 19[7] | 1.0 | 0.1 | 4.0 | 40 | 60 | 65 | 118–178 | 1.3 | 37.7 | 24.3 | 24.0 | 10.9 | 1.2 | 0.6 |
| | 1.0 | | 3.0 | 45–65 | | | | | | | | | | |
| 20[7] | 1.0 | 0.1 | 4.0 | 40–45 | 60 | 65 | 145–180 | 1.9 | 39.0 | 23.2 | 24.3 | 10.3 | 0.8 | 0.5 |
| | 1.0 | | 3.0 | 45–65 | | | | | | | | | | |
| 21[8] | 0.5 | 0.1 | 2.0 | 25–30 | 60 | 65 | 79–131 | 0.8 | 27.6 | 41.3 | 20.1 | 3.6 | N.D. | 6.4 |
| | 1.0 | | 5.0 | 45–65 | | | | | | | | | | |
| 22[9] | 1.0 | 0.1 | 4.0 | 23–30 | 120 | 65 | 130–194 | 4.0 | 67.9 | 20.4 | 6.5 | 1.0 | tr | 0.3 |
| | 0.5 | | 3.0 | 45–65 | | | | | | | | | | |
| 23[10] | 0.6 | 0.1 | 4.0 | 21–32 | 50 | 60–68 | 145–185 | 1.3 | 40.3 | 26.7 | 22.1 | 8.4 | 1.0 | 0.2 |
| | 0.5 | | 3.0 | 49–65 | | | | | | | | | | |

[2]Less than 7.0 moles of bromine per mole of DPE used.
[3]More than 7.0 moles of bromine per mole of DPE used.
[4]The temperature during the ZrCl$_4$ bromination step was higher than 30° C.
[5]Temperature during AlCl$_3$ bromination step was lower than 65° C.
[6]Bromochloromethane used as the solvent during the bromination steps.
[7]The solvent used during the bromination steps was ethylene dibromide.
[8]Insufficient ZrCl$_4$ catalyst was used during the first bromination step.
[9]Insufficient amount of AlCl$_3$ catalyst was used during the second bromination step.
[10]Insufficient amount of catalyst used in each bromination step, Fe° was the first catalyst and AlCl$_3$ was the first bromination catalyst.

EXAMPLE 2

Runs 24–32 (TABLE III) illustrated the bromohomolog distribution obtained when a weaker first or second bromination catalyst was used. In these runs, 0.1 moles of diphenylethane (DPE) were reacted with bromine in the presence of the amount of the catalyst indicated in column 2 of the Table.

TABLE III

| Run No. | Catalyst (grams) | DPE (moles) | Br$_2$/DPE Added (moles) | React. Temp. (°C.) | Ride Time (min.) | Ride Temp. (°C.) | M.P. (°C.) | Br$_5$ | Br$_6$ | GC Area Br$_7$ | Br$_8$ | Percent Br$_9$ | Br$_{10}$ | Light Ends |
|---|---|---|---|---|---|---|---|---|---|---|---|---|---|---|
| 24[11] | 1.3 | 0.1 | 3.0 | 20–32 | 136 | 34–85 | 150–180 | tr | 41.4 | 28.8 | 20.8 | 7.7 | 1.1 | 0.1 |
| | 1.0 | | 3.0 | 31–36 | | | | | | | | | | |
| 25[11] | 1.2 | 0.1 | 4.0 | 24–27 | 158 | 27–74 | — | 0.2 | 45.9 | 23.2 | 19.6 | 9.2 | 1.7 | 0.3 |
| | 0.9 | | 3.0 | 27 | | | | | | | | | | |
| 26[12] | 1.0 | 0.1 | 3.0 | 25–45 | 120 | 55 | 111–140 | 0.2 | 51.5 | 37.5 | 9.7 | 1.0 | tr | 0.1 |
| | 1.0 | | 4.0 | 45–65 | 60 | 65 | | | | | | | | |
| 27[13] | 1.8 | 0.1 | 2.0 | 25–27 | 180 | 70 | 130–190 | 2.3 | 66.0 | 23.6 | 7.3 | 0.7 | tr | 0.2 |
| | | | 2.0 | 40–45 | | | | | | | | | | |
| | | | 3.0 | 65–68 | | | | | | | | | | |
| 28[14] | 1.3 | 0.1 | 4.0 | 25–30 | 120 | 65 | 125–193 | 3.3 | 75.4 | 19.0 | 2.3 | tr | tr | 0.1 |
| | | | 3.0 | 45–65 | | | | | | | | | | |
| 29[14] | 1.7 | 0.1 | 4.0 | 65–70 | 135 | 80 | 148–210 | 0.4 | 36.2 | 31.9 | 22.8 | 7.5 | 1.0 | 0.2 |
| | | | 3.0 | 80 | | | | | | | | | | |
| 30[14] | 1.8 | 0.1 | 3.0 | 40 | 120 | 80 | 135–183 | 0.7 | 38.4 | 31.2 | 21.7 | 6.5 | 0.6 | 0.4 |
| | | | 1.0 | 60 | | | | | | | | | | |
| | | | 3.0 | 80 | | | | | | | | | | |
| 31[15] | 0.9 | 0.1 | 4.0 | 25–45 | 60 | 65 | 81–135 | 0.3 | 16.8 | 36.8 | 29.5 | 8.2 | 0.3 | 8.1 |
| | 1.0 | | 3.0 | 65 | | | | | | | | | | |
| 32[16] | 1.8 | 0.1 | 4.0 | 20–25 | 60 | 20–25 | 143–183 | 3.5 | 54.0 | 20.1 | 16.0 | 5.3 | 0.4 | 0.3 |
| | | | 2.75 | | | | | | | | | | | |

[11]The first bromination catalyst was ZrCl$_4$, and the second bromination catalyst was FeCl$_3$.
[12]The first bromination catalyst was SbCl$_3$, and the second bromination catalyst was AlCl$_3$.
[13]ZrCl$_4$ was the catalyst used in each bromination step.
[14]FeCl$_3$ was the bromination catalyst used in each bromination step.
[15]AlCl$_3$·H$_2$O used as the first bromination catalyst, and AlCl$_3$ used as the second bromination catalyst.
[16]FeBr$_3$ used as the bromination catalyst in each bromination step.

EXAMPLE 3

Polystyrene-based and ABS-based formulations were prepared using a Brabender mixer. The formulations contained 4 weight percent $Sb_2O_3$, 80-85 weight percent of the polystyrene resin indicated; and about 18 weight percent of the flame retardant indicated. Each formulation was compression molded at a temperature of 177° C. and at a molding pressure of 1400-1800 gram-meter torque to form test specimens which are identified in Table 3 in accordance with which formulation was used to produce which specimen.

TABLE IV

|  | Test Plaque 1 | Test Plaque 2 | Test Plaque 3 | Test Plaque 4 |
| --- | --- | --- | --- | --- |
| Formulation |  |  |  |  |
| Saytex ® S-411[1] | 13.0 wt. % | — | — | — |
| Saytex ® S-411[1] | — | 18.7 wt. % | — | — |
| Saytex ® S-411[2] | — | — | 12.5 wt. % | — |
| FF-680[3] | — | — | — | 14.1 wt. % |
| $Sb_2O_3$ | 4.0 wt. % | 4.0 wt. % | 4.0 wt. % | 4.0 wt. % |
| HIPS[4] | 83.0 wt. % | — | 83.5 wt. % | 81.9 wt. % |
| ABS[5] | — | 77.3 wt. % | — | — |
| Physicals |  |  |  |  |
| UL-94 (⅛") | V-0 | V-0 | V-0 | V-2 |
| (1/16") | V-0 | V-0 | V-0 | V-2 |
| LOI | 25.3 | 36.2 | 26.2 | 25.0 |
| HDT (°C.) ⅛" at 264 psi | 69 | 76 | 69 | 63.5 |
| Melt Index (3800 g/230° C.) | 26.8 | 4.0 | 6.0 | 21.4 |
| Izod Impact ⅛" (ft-lb/in notch) | 1.9 | 1.9 | 2.0 | 1.7 |
| $\Delta E_{48}$ (Sunlighter) | 14.3 | 12.3 | 40.0 | 30.7 |
| Hunter Color |  |  |  |  |
| Initial L | 62.62 | — | 90.96 | 90.04 |
| Initial YI | 28.74 | — | 3.67 | 6.54 |
| Final L | 52.03 | — | 61.15 | 70.09 |
| Final YI | 59.02 | — | 66.48 | 57.75 |

[1] Saytex ® S-411 FR-polybromodiphenylethane of Ethyl Corporation having an average of about 7 bromine atoms per molecule
[2] Saytex ® S-111 ® FR-Octobromodiphenyl oxide of Ethyl Corporation
[3] FF-680-bis(tribromophenoxy)ethane of Great Lakes Corporation
[4] HIPS-high impact polystyrene from the Dow Chemical Company
[5] ABS-acrylonitrile-butadiene-styrene of General Electric Company As can be seen from Table IV, the brominated diphenylethane mixtures of this invention (Test Plaques 1 and 2) gave a UL-94 V-0 rating with little adverse affect on the specimen's Izod Impact strength.

What is claimed is:

1. A process for preparing a mixture of brominated non-condensed ring polyaromatics having an average of from about 6 to about 8 bromine atoms per molecule, a low melting point range, and a low amount of light end impurities, which process comprises:
    a) adding a first amount of bromine to a reactor initially containing a reaction mass comprising a solvent, a catalytic amount of a first bromination catalyst, and a non-condensed ring polyaromatic of the formula

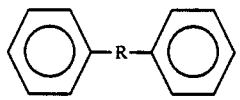

wherein R is an alkylene group of 1 to 10 carbon atoms, an oxygen atoms, a sulfur atom, an oxyalkylene group of up to 6 carbon atoms, an oxyalkyleneoxy group of up to 6 carbon atoms or a carbon single bond;
    b) maintaining the reaction mass during the addition of the first amount of bromine at a first bromination temperature;
    c) terminating the addition of the first amount of bromine when sufficient bromine has been added to obtain the mixture of polyaromatics having an average of about 4 bromine atoms per molecule of polyaromatic;
    d) adding a second bromination catalyst to the mixture;
    e) adding a second amount of bromine to the reaction mass while heating the reaction mass to a second bromination temperature; and,
    f) after at least substantially all of the bromine has reacted, recovering the brominated non-condensed ring polyaromatic mixture from the reaction mass, the recovered mixture containing more than about 35%, based on gas chromatographic area percent, of a brominated polyaromatic having about 7 bromine atoms per molecule.

2. The process of claim 1 wherein the solvent is methylene bromide, methylene chloride or a mixture thereof.

3. The process of claim 1 wherein there are from about 800 mLs to about 1200 mLs of solvent per mole of non-condensed ring polyaromatic.

4. The process of claim 1 wherein the first bromination catalyst is, at least initially, a zirconium tetrachloride catalyst.

5. The process of claim 1 wherein the second bromination catalyst is, at least initially, an aluminum trichloride catalyst.

6. The process of claim 4 wherein the amount of zirconium tetrachloride catalyst is within the range of from about 4 to about 6 wt.% based on the total weight of the non-condensed ring polyaromatic.

7. The process of claim 5 wherein the amount of aluminum trichloride catalyst is within the range of from about 4 to about 6 wt.% based on the total weight of the non-condensed ring polyaromatic.

8. The process for claim 1 wherein the amount of bromine added to the reaction mass is from about 6.75 to about 7.05 moles of bromine per mole of non-condensed ring polyaromatic.

9. The process of claim 1 wherein the non-condensed ring polyaromatic is diphenyl oxide or 1,2-diphenylethane.

10. The process for claim 9 wherein the solvent is methylene bromide, methylene chloride or a mixture thereof.

11. The process of claim 9 wherein the solvent is methylene bromide.

12. The process of claim 9 wherein there are from about 800 mLs to about 1200 mLs of solvent per mole of non-condensed ring polyaromatic.

13. The process of claim 9 wherein the first bromination catalyst is, at least initially, zirconium tetrachloride and the second bromination catalyst is, at least initially, aluminum trichloride and wherein the amount of each of the first and second catalyst added is within the range of from about 4 to about 6 wt.% based on the total weight of the non-condensed ring polyaromatic.

14. The process of claim 13 wherein the first bromination temperature is in a range of from about 15° C. to about 40° C.

15. The process of claim 13 wherein the second bromination temperature is in a range of from about 40° C. to about 70° C.

16. The process of claim 15 wherein the mixture of brominated non-condensed ring polyaromatic is a mixture of brominated b 1,2-diphenylethanes having a melting point in the range of from about 110° C. to about 180° C.

17. The process of claim 1 wherein the non-condensed ring polyaromatic is 1,2-diphenylethane and wherein the recovered mixture contains from about 0 to about 1 wt.% pentabromodiphenylethane; from about 20 to about 30 wt.% hexabromodiphenylethane; from about 35 to about 50 wt.% heptabromodiphenylethane; from about 20 to about 32 wt.% octabromodiphenylethane, from about 2 to about 8 wt.% nonabromodiphenylethane, from about 0 to about 1 wt.% decabromodiphenylethane, and less than about 0.5 wt.% light ends.

18. The process for claim 1 wherein the non-condensed ring polyaromatic is 1,2-diphenylethane and wherein the recovered mixture, when subjected to gas chromatography (GC), will yield a gas chromatogram is which there is indicated from about 0 to about 1 GC area percent pentabromodiphenylethane; from about 20 to about 30 TC area percent hexabromodiphenylethane; from about 35 to about 50 GC area percent heptabromodiphenylethane; from about 20 to about 32 GC area percent octabromodiphenylethane, from about 2 to about 8 GC area percent nonabromodiphenylethane. from about 0 to about 1 GC area percent decabromodiphenylethane, and less than about 0.5 GC area percent light ends.

19. A flame retardant product comprising a mixture of brominated non-condensed ring polyaromatics having an average of about 6-8 bromine atoms per molecule and a melting point range of from about 110° C. to about 180° C.

20. The product of claim 19 the non-condensed ring polyaromatic is 1,2-diphenylethane and wherein the mixture contains from about 0 to about 1 wt.% pentabromodiphenylethane; from about 20 to about 30 wt.% hexabromodiphenylethane; from about 35 to about 50 wt.% heptabromodiphenylethane; from about 20 to about 32 wt.% octabromodiphenylethane, from about 2 to about 8 wt.% nonabromodiphenylethane. from about 0 to about 1 wt.% decabromodiphenylethane, and less than about 0.5 wt. % light ends.

21. The product of claim 19 wherein the non-condensed ring polyaromatic is 1,2-diphenylethane and wherein the mixture, when subjected to gas chromatography (GC), will yield a gas chromatogram in which there is indicated from about 0 to about 1 GC area percent pentabromodiphenylethane; from about 20 to about 30 GC area percent hexabromodiphenylethane; from about 35 to about 50 GC area percent heptabromodiphenylethane; from about 20 to about 32 GC area percent octabromodiphenylethane, from about 2 to about 8 GC area percent nonabromodiphenylethane, from about 0 to about 1 GC area percent decabromodiphenylethane, and less than about 0.5 GC area percent light ends.

22. A flame retardant product comprising a mixture of brominated diphenylethane, wherein the mixture contains from about 0 to about 1 wt.% pentabromodiphenylethane; from about 20 to about 30 wt.% hexabromodiphenylethane; from about 35 to about 50 wt.% heptabromodiphenylethane; from about 20 to about 32 wt.% octabromodiphenylethane, from about 2 to about 8 wt.% nonabromodiphenylethane, from about 0 to about 1 wt.% decabromodiphenylethane, and less than about 0.5 wt.% light ends.

* * * * *